(12) United States Patent
Pavone et al.

(10) Patent No.: US 8,691,221 B2
(45) Date of Patent: *Apr. 8, 2014

(54) ANALGESIC TREATMENT WITH PROLONGED EFFECT

(75) Inventors: Flaminia Pavone, Rome (IT); Sara Marinelli, Rome (IT); Antonio Cattaneo, Trieste (IT); Gabriele Ugolini, Rome (IT)

(73) Assignee: Lay Line Genomics S.p.A., Rome (IT)

( * ) Notice: Subject to any disclaimer, the term of this patent is extended or adjusted under 35 U.S.C. 154(b) by 1152 days.

This patent is subject to a terminal disclaimer.

(21) Appl. No.: 11/921,398

(22) PCT Filed: Jun. 7, 2006

(86) PCT No.: PCT/IT2006/000427
§ 371 (c)(1),
(2), (4) Date: Jul. 13, 2010

(87) PCT Pub. No.: WO2006/131952
PCT Pub. Date: Dec. 14, 2006

(65) Prior Publication Data
US 2010/0291083 A1 Nov. 18, 2010

(30) Foreign Application Priority Data
Jun. 7, 2005 (IT) .............................. RM2005A0290

(51) Int. Cl.
*A61K 39/395* (2006.01)

(52) U.S. Cl.
USPC ..................................... 424/130.1; 530/387.1

(58) Field of Classification Search
None
See application file for complete search history.

(56) References Cited

U.S. PATENT DOCUMENTS

| 5,530,101 | A | * | 6/1996 | Queen et al. | 530/387.3 |
| 5,877,016 | A | | 3/1999 | Presta et al. | |
| 8,296,079 | B2 | | 10/2012 | Cattaneo | |

FOREIGN PATENT DOCUMENTS

| WO | WO/00/73344 | * | 7/2000 |
| WO | WO-00/73344 A | | 12/2000 |
| WO | WO/2005/061540 | * | 7/2005 |
| WO | WO-2005/061540 A | | 7/2005 |
| WO | 2009/098238 | | 8/2009 |

OTHER PUBLICATIONS

Rudikoff et al (Proc Natl Acad Sci USA 1982 vol. 79 p. 1979).*
MacCallum et al. J. Mol. Biol. (1996) 262, 732-745.*
Pascalis et al. The Journal of Immunology (2002) 169, 3076-3084.*
Casset et al. (2003) BBRC 307, 198-205.*
Vajdos et al. (2002) 320, 415-428.*
Wu et al. J. Mol. Biol. (1999) 294, 151-162.*
Chen et al. J. Mol. Bio. (1999) 293, 865-881.*
Covaceuszach Sonia et al: "Neutralization of NGF-TrkA receptor interaction by the novel antagonistic anti-TrkA monoclonal antibody MNAC13: a structural insight." Proteins. Feb. 15, 2005, vol. 58, No. 3, pp. 717-727, XP002338675, ISSN: 1097-0134, the whole document.
McMahon S B et al: "The biological effects of endogenous nerve growth factor on adult sensory neurons revealed by a trkA-IgG fusion molecule." Nature Medicine. Aug. 1995, pp. 774-780, XP009073417, ISSN: 1078-8956, the whole ducment.
Weismann C et al: "Crystal structure of nerve growth factor in complex with the ligand-binding domain of the TrkA receptor" Nature, Nature Publishing Group, London, GB, vol. 401, No. 6749, Sep. 9, 1999, pp. 184-188, XP002961394, ISSN: 0028-0836, the whole document.
Owolabi J B et al: "Characterization of Antiallodynic Actions of ALE-0540, A Novel Nerve Growth Factor Receptor Antagonist, in the Rat" Journal of Pharmacology and Experimental Therapeutics, American Society for Pharmacology and, US, vol. 289, No. 3, Jun. 1999, pp. 1271-1276, XP000980396, ISSN: 0022-3565, the whole document.
Zhu Z et al: "Nerve Growth Factor Expression Correlates With Perineural Invasion and Pain in Human Pancreatic Cancer", Journal of Clinical Oncology, Grune and Stratton, New York, NY, US, vol. 17, No. 8, Aug. 1999, pp. 2419-2428, XP001015680, ISSN: 0732-183X, the whole document.
Indo Y et al; "Mutations in the TRKA/NGF Receptor Gene in Patients With Congenitalinsensitivity to Pain With Anhidrosis", Nature Genetics, New York, NY US, vol. 13, Aug. 13, 1996, pp. 485-488, XP002947157, ISSN: 1061-4036, the whole document.
Jirholt et al., "A central core structure in an antibody variable domain determines antigen specificity." Protein Engineering 14(1): 67-74; 2001.

* cited by examiner

Primary Examiner — Laura B Goddard
Assistant Examiner — Meera Natarajan
(74) Attorney, Agent, or Firm — Saul Ewing LLP; Peter C. Lauro, Esq.

(57) ABSTRACT

Use of an anti-TrkA antibody capable of inhibiting the binding between NGF and TrkA, in particular capable of blocking the biological activity of TrkA, for the preparation of a medicament for treating and/or preventing chronic pain.

14 Claims, 4 Drawing Sheets

ANALGESIC TREATMENT WITH PROLONGED EFFECT

CROSS-REFERENCE TO RELATED APPLICATIONS

Figure 1:
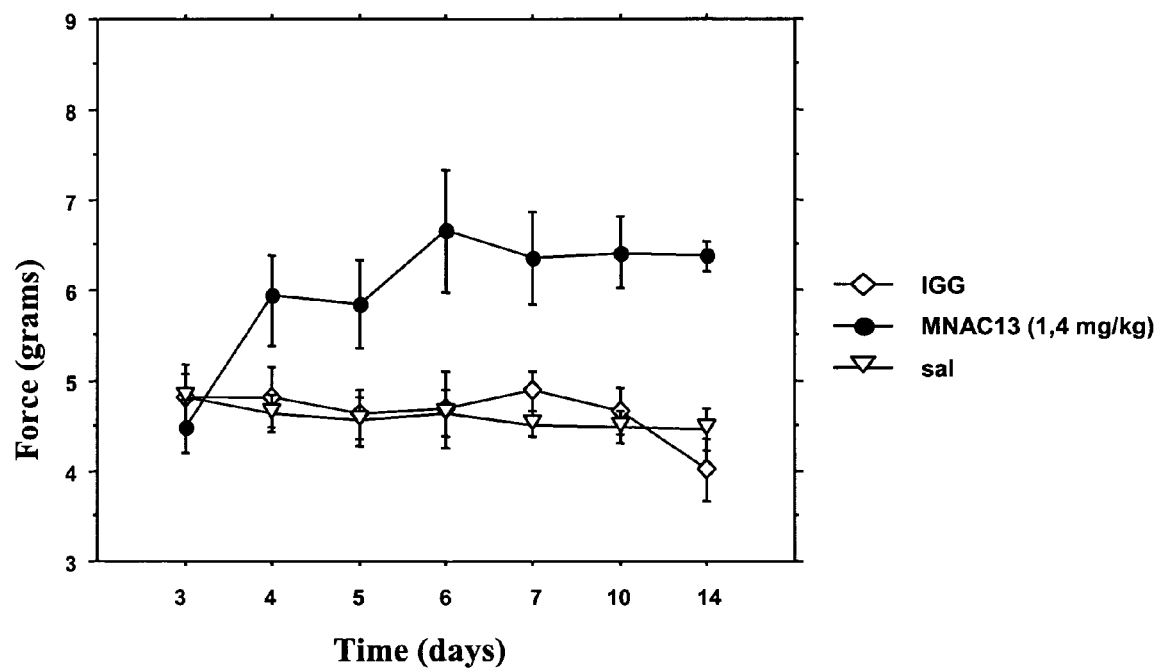

This application is a U.S. national phase application, pursuant to 35 U.S.C. §371, of PCT international application Ser. No. PCT/IT2006/000427, filed Jun. 7, 2006, and published on Dec. 14, 2006, as publication WO2006/131952, which claims priority to IT patent application Ser. No. RM 2005 A 000290, filed Jun. 7, 2005. The entire contents of the aforementioned patent applications are incorporated herein by this reference.

SEQUENCE LISTING

The instant application contains a Sequence Listing which has been submitted via EFS-Web and is hereby incorporated by reference in its entirety. The Sequence Listing, in ASCII format, was created on Jul. 13, 2010, is named 69753USSeq ListingPCT94036ST25.txt and is 16,075 bytes in size.

BACKGROUND TO THE INVENTION

The present invention relates to the use of molecules capable of inhibiting the binding between NGF and its receptor, TrkA. In particular, it relates to antibodies that, by blocking the biological activity of NGF, have a prolonged analgesic effect. Owing to the enduring analgesic effect thereof, they provide an advantageous therapy for pathologies with persistent forms of pain, known also as chronic pain, such as but not limited to neuropathic or oncological pain.

STATE OF THE ART

The nociceptive signals afferent to the spinal cord are carried by the fibres Aδ and C, the cell bodies of which (primary sensitive neurons) are located in the spinal dorsal ganglia (DRG). The primary sensitive neurons release glutamate together with ATP as an excitatory neurotransmitter, and various other substances such as substance P and CGRP (calcitonin-gene-related-peptide), (Hunt and Mantyh, 2001). The release of these excitatory neurotransmitters is controlled by various classes of receptors present on the afferent terminals including those sensitive to capsaicin (vanilloid receptors, VR1), those activated by GABA, those activated by ATP itself and those activated by cannabinoids (CB1) (Sivilotti and Nistri, 1991; Hunt and Mantyh, 2001; Khakh, 2001; Morisset et al., 2001). One of the physiopathological whereby chronic pain occurs is allodynia, i.e. the transformation of stimuli that are not normally painful into painful sensations. This phenomenon involves various ionic currents and therefore different channels of the "ligand-gated" type, including the receptor for the capsaicin, VR1, and the ionotropic receptors for ATP (Khakh, 2001). The simultaneous activation of the receptors for VR1 and of those for ATP on spinal nociceptive interneurons generates a considerable accumulation of the excitatory synaptic signals with reinforcement of the painful stimulus transmission (Nakatsuka et al., 2002). From these observations it is therefore clear that the ATP receptors (especially those belonging to the P2X3 class) play a fundamental role in the pain pathways (Burnstock, 2001). These receptors are present on the peripheral nerve terminals activated by algogenic stimuli, on the cell bodies of the neurons in the DRGs and on the presynaptic terminals thereof, as well as on postsynaptic terminals in the spinal cord (Khakh, 2001).

There is considerable evidence showing an involvement of the nerve growth factor (NGF) and its high-affinity receptor TrkA (Levi-Montalcini, 1987; Levi-Montalcini et al., 1996; Frade and Barde, 1998; Kaplan, 1998) in the molecular processes underlying the main kinds of "persistent" pain, indicating a major therapeutic area (that of pain, with particular reference to the "tonic" forms), for the antibodies which block the NGF/TrkA system (Levine, 1998). The development of sensitive nociceptive neurons depends greatly on NGF, and the responses of the adult nociceptors are modulated by the same factor (Julius and Basbaum, 2001). In particular, NGF exerts acute sensitisation to the capsaicin algogenic stimulus (Shu and Mendell, 1999). From a functional standpoint, nociceptive neurons, following chronic inflammation, develop alterations in the frequency and duration of their action potential. These phenomena regress by blocking endogenous NGF, leading to a significant attenuation of the hyperexcitability typical of states of chronic pain (Djouhri et al., 2001). NGF action in defining the pain threshold in adult nociceptors is mediated by the TrkA receptor, also through modulation of the response mediated by the VR1 receptor present on the nociceptive terminals. The TrkA dependent potentiation of the VR1 response is thought to occur through the intracellular transduction pathway of the phospholipase C gamma ((PLCgamma, Chuang et al., 2001). The peripheral NGF levels are increased in inflammatory processes, while the administration of exogenous NGF has a hyperalgesic effect on rats and produces muscular pain in humans. Furthermore, NGF produces hypersensitisation to heat stimulation in humans and mammals in general. NGF is released by mast cells, fibroblasts and other cell types in the peripheral sites where inflammatory processes occur. In particular, mast cells appear to play a fundamental role (Woolf et al., 1996). As they produce NGF and at the same time express functional TrkA receptors on their surface (Nilsson et al., 1997), they are able to respond to NGF itself, in the presence of lysophosphatidylserine (Horigome et al., 1993; Kawamoto et al., 2002). As a result, the NGF/TrkA system appears to mediate mastocyte activation through an autocrine positive feedback mechanism which allows local amplification of the algogenic inflammatory signal.

High levels of NGF are also found in neurons, where this neurotrophin is apparently responsible for the modifications of the nerve fibres, associated with pain (Harpf et al., 2002). In certain forms of cancer, the excess of NGF facilitates the growth and infiltration of nerve fibres with induction of oncological pain (Zhu et al., 1999). Recent experimental studies demonstrate how, by blocking NGF, it is possible to significantly reduce the formation of neuromas, responsible for neuropathic pain, without damaging the cell bodies of the lesioned neurons (Kryger et al., 2001). These results generated significant interest in therapeutic approaches based on the reduction of NGF effects for the treatment of chronic pain (Saragovi and Gehring, 2000). In recent years, the involvement of the NGF/TrkA system in the molecular processes of pain transduction was also genetically demonstrated. In particular, mutations of the TrkA gene (localised on the chromosome 1q21-q22) are responsible for a hereditary recessive autosomic syndrome known as CIPA ("congenital insensitivity to pain with anhydrosis"), characterised by recurrent episodic fever, anhydrosis, absence of reaction to nociceptive stimuli, mental retardation and a tendency to self-mutilation (Indo et al., 1996; Saragovi and Gehring, 2000; Indo, 2001; Indo et al., 2001). Further confirmation of the involvement of NGF in the nociceptive response was recently obtained by the inventors with the characterisation of anti-NGF transgenic mice phenotype (AD11). In these animals, the ectopic expression of the anti-NGF antibody αD11 produces a functional block of NGF in adult age. Such block consistently translates into an increase in the latency time of the response to harmful heat stimuli (Capsoni et al., 2000; Ruberti et al., 2000). Numerous evidence indicates the system constituted by the nerve growth factor (NGF) and its high-affinity receptor TrkA as a possible target for pain therapy. For this reason, antibodies capable of neutralising the biological activity of the NGF/TrkA system by blocking the TrkA receptor may represent an important resource for pain therapy, in particular for persistent pain.

The authors of the present invention make use of antibodies (directed against the TrkA receptor) which are able to block the biological effects of NGF mediated by TrkA. The reagents MNAC13 is of particular interest.

The MNAC13 antibody is a mouse monoclonal antibody directed against the human TrkA receptor (Cattaneo et al., 1999; Pesavento et al., 2000), particularly effective in the inhibition of TrkA activation by NGF and the downstream biological functions, both in vitro and in vivo (Cattaneo et al., 1999; Pesavento et al., 2000). Anti-TrkA antibodies, including the MNAC13 antibody, having an antagonist activity preventing the functional activation of TrkA by NGF" are disclosed in EP 1.181.318. Derivatives of such antibody are also disclosed in WO2005/061540. However the therapeutic or preventive effect of such molecules on chronic pain is not disclosed.

The antibodies were characterised in detail from the point of view of the structure (Covaceuszach et al., 2001) and from the molecular interaction with the TrkA receptor (Covaceuszach et al., 2005). On the basis of such in-depth structural knowledge, by means of an innovative method a humanised version of MNAC13 was generated (Hu MNAC13), with the same features of antigen binding as the parental antibody (patent application WO2005/061540).

The currently available therapies for the treatment of neuropathic pain, caused by a primary lesion or by a dysfunction of the nervous system, for treatment of oncological pain, and for numerous other forms of persistent pain (also of an inflammatory nature) have been found to be of limited effectiveness. There is a clear need to identify and develop new molecules with analgesic activity, with different mechanism of action compared with drugs currently used in therapy, in order to solve side effects related problems. The international patent application WO 02/20479 discloses small synthetic molecules which, by inhibiting the TrkA receptor, have potential analgesic activity. Nevertheless, the effect of these molecules on certain pain models has not been demonstrated. Furthermore, when compared with antibodies, small molecules have the drawback of being more likely to penetrate the haematoencephalic barrier, with the possibility of serious side effects. In fact, the cholinergic neurons of the basal forebrain, a neuronal population affected by various forms of progressive neurodegeneration, including Alzheimer's disease (Saper et al., 1985), express the TrkA receptor and depend on NGF for correct functioning (Holtzman et al., 1992). The international patent application WO 01/78698 proposes the use of an NGF antagonist for preventing or treating chronic visceral pain, but not neuropathic or oncological pain. Although the application states that the antagonist can bind both NGF and the TrkA receptor, it is not demonstrated that upon binding of the antagonist to TrkA the receptor is functionally blocked.

Based on the ability of MNAC13 antibody to block the biological activity of NGF/TrkA, the antibody and its humanised versions were tested in various animal models of persistent pain, in particular in the "Chronic Constriction Injury"

model (CCI, chronic constriction injury of the sciatic nerve), for assessment of chronic pain of neuropathic nature (Bennett and Xie, 1988).

SUMMARY OF THE INVENTION

The object of the present invention is the use of an anti-TrkA antibody that is able to inhibit the binding between NGF and TrkA, for the preparation of a medicament for the treatment of chronic pain.

Suitably the antibody blocks the biological activity of TrkA i.e. is an antagonistic antibody.

A molecule that blocks the biological activity of TrkA refers to a molecule that acts as an antagonist in terms of the NGF binding to the TrkA receptor, and which can be defined as a synthetic molecule or a monoclonal antibody or a biological/synthetic derivative thereof which:

i) binds to TrkA; and
ii) inhibits the binding of NGF to the "native" TrkA receptor expressed on the surface of living cells; and
iii) blocks the biological activity deriving from NGF binding to the same TrkA receptor.

The term "blocking the biological activity" does not simply mean blocking activation of the receptor, defined as blocking the conversion process of the receptor itself into an "active" state, but also the functional neutralisation of biological consequences downstream of the activation process: second messengers, new gene expression, phenotypic and functional modifications both at cell and system level. The molecule of the invention is not only able to block TrkA in a classic in vitro test (test of neuritic growth in PC12 cells), but also in vivo (functional block of the cholinergic neurons of the basal forebrain and block of the nociception in a classic "hot plate" test).

As noted above antagonistic TrkA antibodies are disclosed in EP 1181318 and in WO 2005/061540.

Therefore it is an object of the invention the use of an anti-TrkA antibody capable of inhibiting the binding between NGF and TrkA for the preparation of a medicament for treating and/or preventing chronic pain. Suitably the antibody is capable of blocking the biological activity of TrkA.

There is also provided as an aspect of the invention a method of treatment and/or prevention of chronic pain in a subject comprising administering to the subject an effective amount of an anti-TrkA antibody thereby to treat and/or prevent chronic pain in said subject. There is also provided a kit comprising a composition containing an anti-TrkA antibody together with instructions directing administration of said composition to a subject in need of treatment and/or prevention of chronic pain thereby to treat and/or prevent chronic pain in said subject.$_{[AJT1]}$ In an aspect of the invention the variable region of the antibody light chain comprises at least one of the complementarity determining regions (CDRs) having the sequence selected from aa. 24 to aa. 33 of SEQ ID No.1; from aa. 49 to aa. 55 of SEQ ID No. 1; from aa. 88 to aa. 96 of SEQ ID No. 1, more preferably two of the above CDRs, most preferably three of the above CDRs. The variable region of the antibody light chain may, for example, comprise essentially the sequence of SEQ ID No.1.$_{[AJT2]}$ (SEQ ID No. 1)

CDR L1
DIVLTQSPAIMSASLGEEVTLTC<u>SASSSVSYMH</u>WYQQKSGTSPKLLIY

CDR L2                              CDR L3
<u>TTSNLAS</u>GVPSRFSGSGSGTFYSLTISSVEAEDAADYYS<u>HQWSSYPWTF</u>

GGGTKLEIK.

In an aspect of the invention the variable region of the antibody heavy chain comprises at least one of the complementarity determining regions (CDRs) having the sequence selected from aa. 26 to aa. 35 of SEQ ID No. 2; from aa. 50 to aa. 66 of SEQ ID No. 2; from aa. 99 to aa. 112 of SEQ ID No. 2, more preferably two of the above CDRs, most preferably three of the above CDRs. The variable region of the antibody light chain may, for example, comprise essentially the sequence of SEQ ID No.2._[AJT3]

```
                                            (SEQ ID No. 2)
                      CDR H1
EVKLVESGGGLVQPGGSLKLSCAASGFTFSTYTMSWARQTPEKRLEWVA

CDR H2
YISKGGGSTYYPDTVKGRFTISRDNAKNTLYLQMSSLKSEDTALYYCAR

CDR H3
GAMFGNDFFFPMDRWGQGTSVTVSS.
```

The antibody may be in single chain form and comprises a light chain variable region and a heavy chain variable region joined by a linker.

Alternatively the antibody may comprise two light chains and two heavy chains.

In a preferred aspect of the invention the anti-TrkA antibody is a human or humanised antibody. The skilled in the art shall select the proper humanisation method to design the antibody, a preferred method is the method as disclosed in WO 2005/061540. Exemplary humanised antibodies comprise a light chain variable region which is a humanised derivative of SEQ ID No 1 (a mouse origin sequence). Exemplary humanised antibodies comprise a heavy chain variable region which is a humanised derivative of SEQ ID No 2 (a mouse origin sequence)._[AJT4]

In a preferred aspect of the invention the variable region of the humanised antibody light chain comprises essentially the sequence from aa. 1 to aa. 106 of SEQ ID No. 3.

In a more preferred aspect the humanised antibody light chain has essentially the sequence of SEQ ID No. 3.

```
                                            (SEQ ID No. 3)
DIVLTQSP*SSL*SAS*V*Q*D*RVT*I*TCSASSSVSYMHWYQQ*K*P*Q*APKLLIYT

TSNLASGVPSRFSGSGSGT*D*Y*T*LTISS*L*QP ED*V*A*T*YYCHWSSYPWTFGG

GTK*V*EIKRTVAAPSVFIFPPSDEQLKSGTASVVCLLNNFYPREAKVQWK

VDNALQSGNSQESVTEQDSKDSTYSLSSTLTLSKADYEKHKVYACEVTH

QGLSSPVTKSFNRGEC hMNAC13 Vk hCk.
```

In a preferred aspect of the invention the variable region of the humanised antibody heavy chain comprises essentially the sequence from aa. 1 to aa. 123 of SEQ ID No. 4.

In a more preferred aspect the humanised antibody heavy chain has essentially a sequence selected from SEQ ID No. 4, SEQ ID No. 5, SEQ ID No. 6.

```
                                            (SEQ ID No. 4)
EV*Q*LLESGGGLVQPGGS*I*RLSCAASGFTFSTYTMSWARQ*A*P*G*KGLEWVA*Y*
ISKGGGSTYYPDTVKGRFTISRDN*S*KNTLYLQM*N*SI*R*AE*D*S*A*V*YYCAR*G*A*
MFGNDFFFPMDRWGQGT*L*VTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREE
EQYNSTYRVVSVLTVLHQDWLNGKEYKCKVSNKALPAPIEKTISKAKGQP
REPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSL
SPGK hMNAC13 VH hIgG1.
```

```
                                            (SEQ ID No. 5)
EV*Q*LLESGGGLVQPGGS*I*RLSCAASGFTFSTYTMSWARQ*A*P*G*KGLEWVA*Y*
ISKGGGSTYYPDTVKGRFTISRDN*S*KNTLYLQM*N*SI*R*AE*D*S*A*V*YYCAR*G*A*
MFGNDFFFPMDRWGQGT*L*VTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREE
QYASTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLS
PGK hMNAC13 VH hIgG1 (N297A).
```

```
                                            (SEQ ID No. 6)
EV*Q*LLESGGGLVQPGGS*I*RLSCAASGFTFSTYTMSWARQ*A*P*G*KGLEWVA*Y*
ISKGGGSTYYPDTVKGRFTISRDN*S*KNTLYLQM*N*SI*R*AE*D*S*A*V*YYCAR*G*A*
MFGNDFFFPMDRWGQGT*L*VTVSSASTKGPSVFPLAPCSRSTSESTAALGC
LVKDYFPEPVTVSWNSGALTSGVHTFPAVLQSSGLYSLSSVVTVPSSSLG
TKTYTCNVDHKPSNTKVDKRVESKYGPPCPSCPAPEFLGGPSVFLFPPKP
KDTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREPQ
VYTLPPSQEEMTKNQVSLTCLVKGFYPSDIAVEWESNGQPENNYKTTPPV
LDSDGSFFLYSRLTVDKSRWQEGNVFSVSVMHEALHNHYTQKSLSLSLGK
hMNAC13 VH hIgG4.
```

Italics: variable regions, Bold: mutations in the mouse sequence in the humanization process, Underlined: CDRs.

A still further object of the present invention is the use of a molecule that is able to inhibit the binding between NGF and TrkA and to block the biological activity of the latter to prepare a remedy for the treatment of inflammatory chronic pain. More preferably the pain is caused by pancreatitis, kidney stones, headaches, dysmenorrhoea, musculoskeletal pain, sprains, visceral pain, ovarian cysts, prostatitis, cystitis, interstitial cystitis, post-operative pain, migraine, trigeminal neuralgia, pain from burns and/or wounds, pain associated with trauma, neuropathic pain, pain associated with musculoskeletal diseases, rheumatoid arthritis, osteoarthritis, ankylosing spondilitis, periarticular pathologies, oncological pain, pain from bone metastases, pain from HIV. According to International Association for the Study of Pain (IASP, www.iasp-pain.org <http://www.iasp-pain.org/>), pain is generally defined as "An unpleasant sensory and emotional experience associated with actual or potential tissue damage, or described in terms of such damage or both". The essential element in all forms of pain is the activation of specialized high-threshold receptors and nerve fibers to warn the organism of potential tissue damage. The involvement of inflammatory cells and processes is a common element in many pain states. The term "acute pain" means immediate, generally high threshold, pain brought about by injury such as a cut, crush, burn, or by chemical stimulation. The term "chronic pain," as used herein, means pain other than acute pain. It is understood that chronic pain often is of relatively long duration, for example, months or years and can be continuous or intermittent.

The anti-TrkA antibody of the invention is suitably administered systemically. Systemic administration can be performed by injection, e.g. continous intravenous infusion, bolus intravenous infusion, subcutaneous or intramuscular injection. Alternatively other forms of administration (e.g. oral, mucosal, via inhalation, sublingually, etc.) may also be used. Local delivery of the antibody can be performed by local administration eg intra-articular injection or subcutaneous, intramuscular injection in the vicinity of affected tissues.

The anti-TrkA antibody will suitably be formulated in a pharmaceutical composition appropriate for the intended route of administration. Solutions for injection will suitably contain the antibody dissolved or dispersed in an aqueous medium (eg water for injection) as appropriate containing appropriate buffers and molarity modifiers eg phosphate, salt and/or dextrose.

Treatment regimen i.e. dose, timing and repetition, can be represented by single or repeated administrations (eg injections) of the product by the chosen administration route. The interval of dose administration can be subject to modifications depending on the extent and duration of the clinical response, as well as the particular individual and the individual clinical history. Suitably the anti-TrkA antibody has a long duration of action. In particular the clinical effect of the antibody extends following administration may be as long as 21 days as determined from animal studies. Furthermore preliminary data implies that anti-TrkA antibodies may manifest clinical benefit for a longer period than that in which its presence can be detected in a relevant biological matrix such as serum or plasma following its administration. In light of the intended long duration of action (i.e. an effect suitably lasting at least one week, or preferably at least two weeks eg at least three weeks or at least four weeks), suitably the antibody may be administered to subjects at a frequency of not more than once per week eg not more than once per two weeks or once per three weeks or once$_{[AJT5]}$ per four weeks.

A suitable dose of the anti-TrkA antibody will typically range from 0.1 mg/kg to 10 mg/kg body weight Novel antibodies and compositions containing them disclosed herein are claimed as an aspect of the invention.$_{[AJT6]}$ Non-limitative embodiments of the present invention will now be disclosed, with particular reference to the following figures:

FIG. 1: Effect of the anti-TrkA monoclonal antibody MNAC13 (1.4 mg/kg) on neuropathic pain: mechanical allodynia measured by means of a plantar dynamic aesthesiometer; CD1 mice subjected to chronic constriction of the sciatic nerve; the antibodies are injected I.P. at days 3, 4, 5, 6 after lesion of the sciatic nerve. Observation period: from day 3 to day 14. As a negative control, both saline (sal) and mouse immunoglobulins (IgG, 1.4 mg/kg) were used. Results are expressed in terms of absolute value (grams) of the threshold force for the hindpaw ipsilateral to lesion. The values are subjected to statistical analysis by means of analysis of variance (ANOVA) for repeated measurements, in which both the "treatment" factor and the repeated measurement (days) were significant with $p<0.01$ (at least). The animals treated with anti-TrkA or anti-NGF are significantly different from the controls, from day 4 to day 14.

Figure 2:
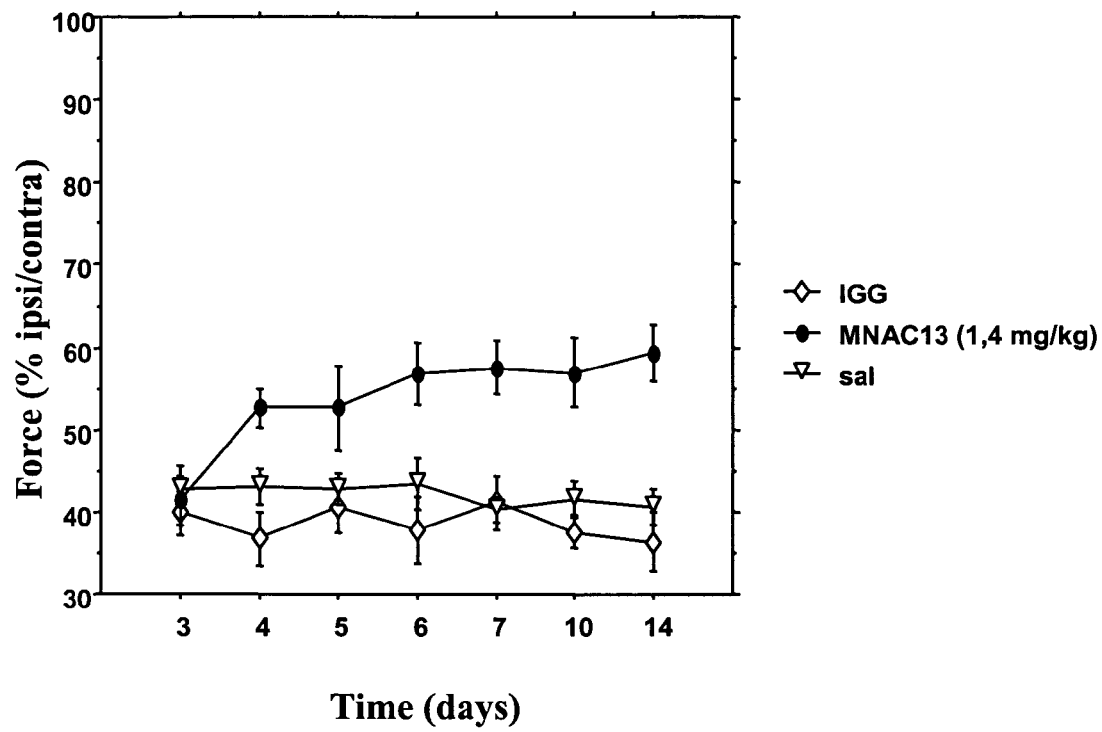

FIG. 2: Effect of the anti-TrkA monoclonal antibody MNAC13 (1.4 mg/kg) on neuropathic pain: mechanical allodynia measured by means of a plantar dynamic aesthesiometer; CD1 mice subjected to chronic constriction of the sciatic nerve; the antibodies were injected I.P. at days 3, 4, 5, 6 after lesion of the sciatic nerve. Observation period: from day 3 to day 14. As a control, both saline (sal) and mouse immunoglobulins (IgG, 1.4 mg/kg) are used. Results were expressed as a percentage, % (ratio between the threshold force of the hindpaw ipsilateral to lesion and that corresponding to the contralateral hindpaw). The corresponding absolute values were subjected to statistical analysis by means of an analysis of the variance (ANOVA) for repeated measurements, in which both the "treatment" factor and the repeated measurement (days) were significant with $p<0.01$ (at least). The animals treated with anti-TrkA were significantly different from the controls from day 4 to day 14.

Figure 3:
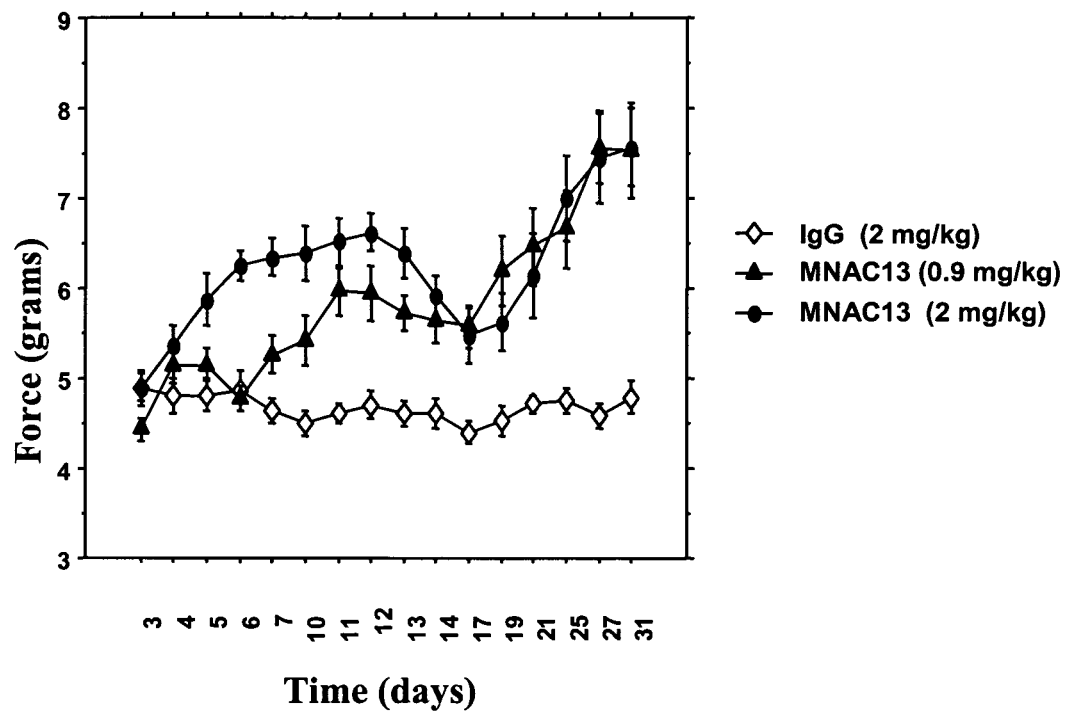

FIG. 3: Effect of the anti-TrkA monoclonal antibody MNAC13 (2 doses: 0.9 and 2 mg/kg) on neuropathic pain: mechanical allodynia measured by means of a plantar dynamic aesthesiometer; CD1 mice subjected to chronic constriction of the sciatic nerve; the antibodies were injected I.P. at days 3, 4, 5, 6, 7, 8, 9, 10 after lesion of the sciatic nerve. Observation period: from day 3 to day 31. As a negative control, mouse immunoglobulins were used (IgG, 2 mg/kg). Results were expressed in terms of the absolute value (grams) of the threshold force for the hindpaw ipsilateral to lesion. The values were subjected to statistical analysis by means of analysis of variance (ANOVA) for repeated measurements, in which both the "treatment" factor and the repeated measurement (days) were significant with $p<0.01$ (at least). The animals treated with MNAC13 were significantly different from the controls up to the last day of observation (31), from day 5 (greater dose of antibody) or from day 7 (lesser dose).

Figure 4:
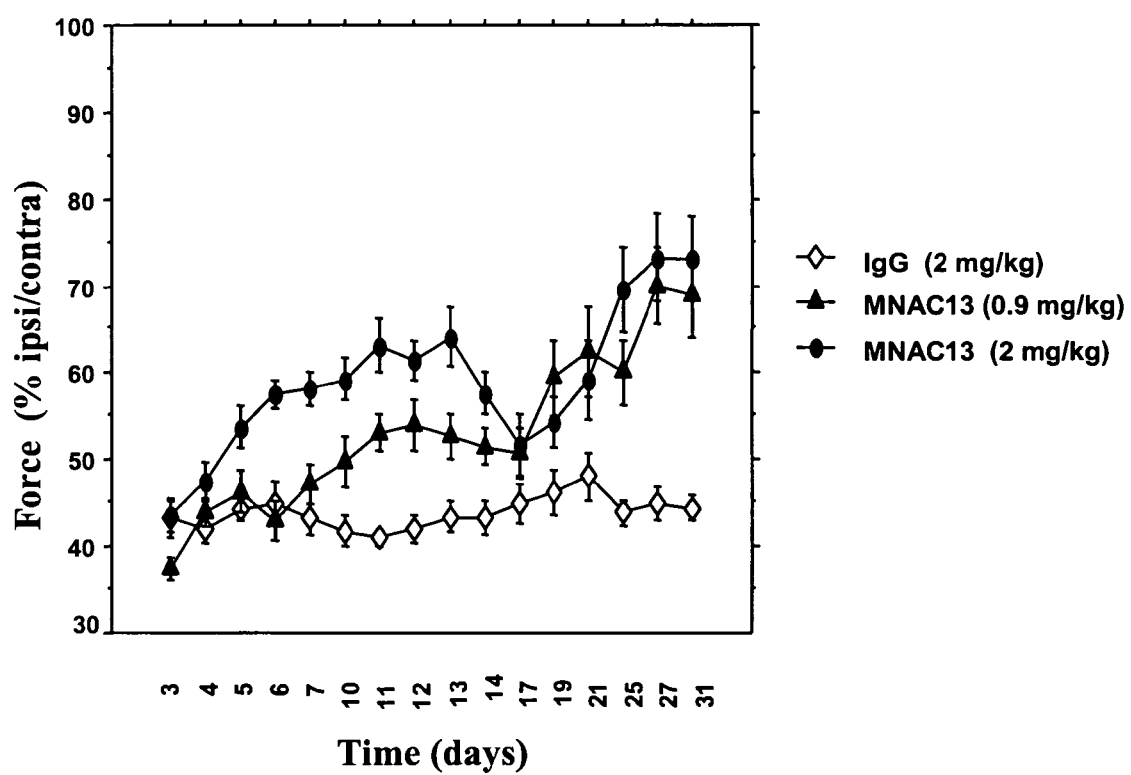

FIG. 4: Effect of the anti-TrkA monoclonal antibody MNAC13 (2 doses: 0.9 and 2 mg/kg) on neuropathic pain: mechanical allodynia measured by means of a plantar dynamic aesthesiometer; CD1 mice subjected to chronic constriction of the sciatic nerve; the antibodies were injected I.P. at days 3, 4, 5, 6, 7, 8, 9, 10 after lesion of the sciatic nerve. Observation period: from day 3 to day 31. As a control, mouse immunoglobulins were used (IgG, 2 mg/kg). Results were expressed as a % (ratio between the threshold force for the hindpaw ipsilateral to lesion and that corresponding to the contralateral hindpaw). The corresponding absolute values were subjected to statistical analysis by means of analysis of variance (ANOVA) for repeated measurements, in which both the "treatment" factor and the repeated measurement (days) were significant with $p<0.01$ (at least). The animals treated with MNAC13 were significantly different from the controls until the last day of observation (31), from day 5 (greater dose of antibody) or from day 7 (lesser dose).

METHODS

Production of Monoclonal Antibodies

The monoclonal antibody MNAC13 (variable region light chain SEQ ID No. 1; variable region heavy chain SEQ ID No. 2) may be produced from a hybridoma supernatant, according to standard methods, disclosed above (Galfre and Milstein, 1981; Cattaneo et al., 1988; Cattaneo et al., 1999). The supernatant containing each antibody was subjected to precipitation (29% ammonium sulphate), followed by dialysis against PBS 1× (Spectra-Por 12/14K membrane, Spectrum) and affinity chromatography on sepharose protein G column (4-Fast Flow, Amersham Biosciences). Elution occurred by means of a low pH (HCl 5 mM) solution that was neutralised upon collection. The final eluate was concentrated (Amicon Ultra-15, 50K, Millipore) to obtain preparations of purified antibody in concentrations between 1 and 5 mg/ml. As far as the humanised versions (IgG1 human) of the antibody (Hu-MNAC13) is concerned, they were also purified as disclosed above, starting from the supernatants of stably transfected CHO cell lines, which are stable cotransfectants for the heavy chain (pVH/CMVexpress) and the light chain (pVL/CMVexpress) of each antibody. Vectors are known in the art, i.e as disclosed in WO 02/096458. The stable cotransfecting clones were obtained through double selection with G418 and mycophenolic acid.

Experiments in Murine Pain Models

The animals were treated and handled in accordance with the guidelines of the IASP Ethical Committee and the Italian national law (DL116/92, application of European Direction 86/609/EEC) on the use of animals in research. Every necessary effort was made to minimise the suffering of the animals and to use the minimum amount of animals required to produce reliable scientific data.

Sciatic Nerve Surgery

Male CD1 mice, weighing approximately 35 g, were anaesthetised (intraperitoneal injection with 500 mg/kg chloral hydrate), the sciatic nerve of the right hind paw was exposed to be subjected to undergo loose ligature by means of stitching thread according to the chronic constriction lesion model (CCI) of the sciatic nerve, disclosed by Bennett and Xie (1988). The loose ligature of the sciatic nerve, inside the upper portion of the thigh, induced peripheral mononeuropathy characterised by thermal/mechanical allodynia and hyperalgesia. By ligation of the nerve at 3 different but close points, the neuropathy was fully developed 3 days following the lesion and lasted for 2-3 months.

Pharmacological Treatment

From the third day following the lesion, anti-TrkA (MNAC13) antibodies were administered in an entire form (Mab) that were diluted in saline solution (vehicle), as indicated in Table I. As controls mouse immunoglobulin was used (IgG), in the same dose as the blocking antibodies (at the greater dose if 2 doses were used), or saline solution. Each experimental group included N=10 animals (unless explicitly stated otherwise).

TABLE I

Administration protocols and measurement of mechanical allodynia.

| Antibody | Dose | Administration i.p. | Allodynia measurement |
|---|---|---|---|
| MNAC 13 | 50 μg/mouse = 1.4 mg/kg | 4, at days 3, 4, 5, 6 after lesion | Days 3 to 14 |
| MNAC 13 | 70 μg/mouse = 2 mg/kg | 8, at days 3, 4, 5, 6, 7, 8, 9, 10 after lesion | Days 3 to 31 |
| MNAC 13 | 30 μg/mouse = 0.9 mg/kg | | |

Mechanical allodynia was measured by means of a plantar dynamic aesthesiometer (Ugo Basile), as indicated in Table I. Day 3 was considered the baseline.

The same protocols were used to assess the analgesic action of the humanised versions of the antibody MNAC13.

Statistical Analysis

The results were expressed in 2 different ways, both as an absolute value of the threshold force value (in grams) that was sufficient for the animal to retract the hind leg that is ipsilateral to the lesion, or in percentage value, as the ratio between the absolute values of the hind legs (ipsilateral/contralateral). The values were subjected to statistical analysis by means of an analysis of the variance (ANOVA) for repeated measurements, in which both the "treatment" factor and the repeated measurement (days) were significant with $p<0.01$.

Model of Chronic Inflammatory Pain

Adjuvant induced arthritis is elicited in male Lewis rats (175-200 g, 7-8 weeks) by injection of 0.1 ml of *Mycobacterium butyricum* in mineral oil into the base of the tail. (Taurog et al., 1988; Devesa et al., 2005). On day 14 arthritic rats are qualified for the study if they show symptoms of the disease, measured as presence of redness, an increase of both hind paw oedema, and an increase in the vocalization after flexion of the ankle.

MNAC13 antibody (2 mg/kg in sterile saline vehicle) is administered twice intravenously, at 14 and 20 days after induction of arthritis. Indomethacin (3 mg/kg) is used as a reference compound and administered orally every day starting from 14 days and up to 20 days after disease induction. Control animals do not receive any treatment. The level of statistical significance was determined by analysis of variance (ANOVA) followed by Dunnett's t-test for multiple comparisons. P values of $p<0.05$ (*) or $p<0.01$ (**) were taken as significant. Data represent mean±S.E.M. (n=7). *$p<0.05$; **$p<0.01$ compared with control group (arthritic rats).

Results

Neuropathic Pain

The results on the CCI model showed that the blocking antibody MNAC13 (FIG. 1 and FIG. 2) had a significant analgesic effect. In particular, a similar result was observed for the two antibodies at the 1.4 mg/kg dose. As shown in FIG. 3 and FIG. 4, they started to have an analgesic effect from the second day of administration (day 4), reaching the maximum effect around day 6, keeping substantially the same analgesic efficacy for the entire duration of the observation until day 14. Expressing the result in percentage terms (ratio between the threshold force for the hindpaw ipsilateral to the lesion and that corresponding to the controlateral hindpaw), as in FIG. 4, it can be stated that for each of the two blocking antibodies, the maximum percentage value was around 60%, being around 40% for the control groups (IgG and saline).

When the animals were observed for 4 weeks, up to day 31, administration of the antibody MNAC 13 (FIG. 3 and FIG. 4) revealed a two-phase effect. The first phase of analgesic efficacy (from day 3 to day 17, i.e. until a week after the last injection) was characterised by a maximum effect around days 11-12 (FIG. 3). This effect was clear for both the doses used (0.9 and 2 mg/kg) although the analgesic efficacy of the lesser dose always remained lower than that of the greater dose. After a reduction of the effect to day 17 (nevertheless still statistically distinguishable from the controls), a second analgesic phase was observed with an increase in the effect up to day 31. The final percentage (day 31) was close to 70% and 65% for the doses of 2 and 0.9 mg/kg, respectively, compared with the percentage value of the control groups around 40% (FIG. 4). Two phases in the analgesic action of MNAC 13 can thus be distinguished: the first ("pharmacological" effect), that comprises the treatment period and the first week after the last injection of antibody (the week during which the effect diminishes, parallel to the haematic concentration of the antibody); the second, which identifies a long-term effect, probably requiring new gene transcription gene expression, which is an effect that gives MNAC 13 the unique feature (in the field of neuropathic pain) of being a "disease-modifying" active principle, i.e. capable of modifying in depth the course of the disease, unlike the products currently used in this therapeutical context, which demonstrate a simple pharmacological effect on the symptoms. Substantially identical results to those illustrated above were obtained when instead of the antibody MNAC13, some humanised versions were used (dose used: 2 mg/kg for each antibody), confirming that the latter have the same analgesic properties as the parental version. The antibody was humanised with the method of WO2005/061540, both at the light (SEQ ID No. 3) and the heavy chain (SEQ ID No. 4) variable regions. To construct whole humanised antibodies, different constant regions were utilised, as above described (SEQ ID No. 3-6).

BIBLIOGRAPHY

Bennett G J, Xie Y K (1988). Pain 33:87-107.
Berardi N, Cellerino A, Domenici L, Fagiolini M, Pizzorusso T, Cattaneo A, Maffei L (1994) Proc Natl Acad Sci USA 91:684-688.
Burnstock G (2001) Trends Pharmacol Sci 22:182-188.
Capsoni S, Ugolini G, Comparini A, Ruberti F, Berardi N, Cattaneo A (2000) Proc Natl Acad Sci USA 97:6826-6831.

Cattaneo A, Rapposelli B, Calissano P (1988) J Neurochem 50:1003-1010.
Cattaneo A, Capsoni S, Margotti E, Righi M, Kontsekova E, Pavlik P, Filipcik P, Novak M (1999) J Neurosci 19:9687-9697.
Chuang H H, Prescott E D, Kong H, Shields S, Fjord S E, Basbaum A I, Chao M V, Julius D (2001) Nature 411:957-962.
Covaceuszach S, Cattaneo A, Lamba D (2001) Acta Crystallogr D Biol Crystallogr 57:1307-1309.
Covaceuszach S, Cattaneo A, Lamba D (2005) Proteins 58:717-727.
Djouhri L, Dawbarn D, Robertson A, Newton R, Lawson S N (2001) J Neurosci 21:8722-8733.
Frade J M, Barde Y A (1998) Bioessays 20:137-145.
Galfre G, Milstein C (1981) Methods Enzymol 73:3-46.
Gonfloni S (1995) Recombinant antibodies as structural probes for neurotrophins. SISSA PhD Thesis.
Harpf C, Dabernig J, Humpel C (2002) Muscle Nerve 25:612-615.
Hempstead B L (2002) Curr Opin Neurobiol 12:260-267.
Holtzman D M, Li Y, Parada L F, Kinsman S, Chen C K, Valletta J S, Zhou J, Long J B, Mobley W C (1992) Neuron 9:465-478.
Horigome K, Pryor J C, Bullock E D, Johnson E M, Jr. (1993) J Biol Chem 268:14881-14887.
Hunt S P, Mantyh P W (2001) Nat Rev Neurosci 2:83-91.
Indo Y (2001) Hum Mutat 18:462-471.
Indo Y, Tsuruta M, Hayashida Y, Karim M A, Ohta K, Kawano T, Mitsubuchi H, Tonoki H, Awaya Y, Matsuda I (1996) Nat Genet 13:485-488.
Indo Y, Mardy S, Miura Y, Moosa A, Ismail E A, Toscano E, Andria G, Pavone V, Brown D L, Brooks A, Endo F, Matsuda I (2001) Hum Mutat 18:308-318.
Julius D, Basbaum A I (2001) Nature 413:203-210.
Kaplan D R (1998) Prog Brain Res 117:35-46.
Kawamoto K, Aoki J, Tanaka A, Itakura A, Hosono H, Arai H, Kiso Y, Matsuda H (2002) J Immunol 168:6412-6419.
Khakh B S (2001) Nat Rev Neurosci 2:165-174.
Kryger G S, Kryger Z, Zhang F, Shelton D L, Lineaweaver W C, Buncke H J (2001) J Hand Surg [Am] 26:635-644.
Lee R, Kermani P, Teng K K, Hempstead B L (2001) Science 294:1945-1948.
Levi-Montalcini R (1987) Science 237:1154-1162.
Levi-Montalcini R, Skaper S D, Dal Toso R, Petrelli L, Leon A (1996) Trends Neurosci 19:514-520.
Levine J D (1998) Neuron 20:649-654.
Molnar M, Ruberti F, Cozzari C, Domenici L, Cattaneo A (1997) Neuroreport 8:575-579.
Molnar M, Tongiorgi E, Avignone E, Gonfloni S, Ruberti F, Domenici L, Cattaneo A (1998) Eur J Neurosci 10:3127-3140.
Morisset V, Ahluwalia J, Nagy I, Urban L (2001) Eur J Pharmacol 429:93-100.
Nakatsuka T, Furue H, Yoshimura M, Gu J G (2002) J Neurosci 22:1228-1237.
Nilsson G, Forsberg-Nilsson K, Xiang Z, Hallbook F, Nilsson K, Metcalfe D D (1997) Eur J Immunol 27:2295-2301.
Porro C A, Cavazzuti M (1993) Spatial and temporal aspects of spinal cord and brainstem activation in the formalin pain model. Prog Neurobiol 41: 565-607.
Pesavento E, Margotti E, Righi M, Cattaneo A, Domenici L (2000) Neuron 25:165-175.
Ruberti F, Capsoni S, Comparini A, Di Daniel E, Franzot J, Gonfloni S, Rossi G, Berardi N, Cattaneo A (2000) J Neurosci 20:2589-2601.
Saper C B, German D C, White C L, 3rd (1985) Neurology 35:1089-1095.
Saragovi H U, Gehring K (2000) Trends Pharmacol Sci 21:93-98.
Sevcik M A, Ghilardi J R, Peters C M, Lindsay T H, Halvorson K G, Jonas B M, Kubota K, Kuskowski M A, Boustany L, Shelton D L, Mantyh P W (2005) Pain 115:128-141.
Shu X, Mendell L M (1999) Neurosci Lett 274:159-162.
Sivilotti L, Nistri A (1991) Prog Neurobiol 36:35-92.
Woolf C J, Ma Q P, Allchorne A, Poole S (1996) J Neurosci 16:2716-2723.
Zhu Z, Friess H, diMola F F, Zimmermann A, Graber H U, Korc M, Buchler M W (1999) J Clin Oncol 17:2419-2428.

---

The invention claimed is:

1. A method for treating and/or preventing chronic pain in a subject comprising administering to a subject in need thereof a therapeutically effective amount of a humanized anti-TrkA antibody capable of inhibiting the binding between nerve growth factor (NGF) and TrkA, wherein the variable region of the antibody light chain comprises the sequence of SEQ ID NO:1 comprising all three complementarity determining regions (CDRs) having a sequence selected from aa. 24 to aa. 33 of SEQ ID NO: 1; from aa. 49 to aa. 55 of SEQ ID NO: 1; and from aa. 88 to aa. 96 of SEQ ID NO:1; and wherein the variable region of the antibody heavy chain comprises essentially the sequence of SEQ ID NO: 2 comprising all three of the complementarity determining regions (CDRs) having a sequence selected from aa. 26 to aa. 35 of SEQ ID NO: 2; from aa. 50 to aa. 66 of SEQ ID NO: 2; from aa. 99 to aa. 112 of SEQ ID NO: 2; and variants of the sequence from aa. 99 to aa. 112 of SEQ ID NO: 2, thereby treating and/or preventing chronic pain in said subject.

2. The method according to claim 1, wherein the antibody is capable of blocking the biological activity of TrkA.

3. The method according to claim 1, wherein the antibody is in single chain form and comprises a light chain variable region and a heavy chain variable region joined by a linker.

4. The method according to claim 1, wherein the antibody comprises two light chains and two heavy chains.

5. The method according to claim 1, wherein the variable region of the humanized antibody light chain comprises essentially the sequence from aa. 1 to aa. 106 of SEQ ID NO: 3.

6. The method according to claim 1, wherein the variable region of the humanized antibody heavy chain comprises essentially the sequence from aa. 1 to aa. 123 of SEQ ID NO: 4.

7. The method according to claim 1, wherein the humanized antibody light chain has essentially the sequence of SEQ ID NO: 3.

8. The method according to claim 1, wherein the humanized antibody heavy chain has essentially a sequence selected from SEQ ID NO: 4, SEQ ID NO: 5 and SEQ ID NO: 6.

9. The method according to claim 1, wherein the pain is of the chronic inflammatory type.

10. The method according to claim 9, wherein the chronic pain is caused by pancreatitis, kidney stones, headaches, dysmenorrhoea, musculoskeletal pain, sprains, visceral pain, ovarian cysts, prostitis, cystitis, interstitial cystitis, post-operative pain, migraine, trigeminal neuralgia, pain from burns and/or wounds, pain associated with trauma, neuropathic pain, pain associated with musculoskeletal diseases, rheumatoid arthritis, osteoarthritis, ankylosing spondilitis, periarticular pathologies, oncological pain, pain from bone metastases, pain from HIV.

11. The method according to claim 1, wherein the pain is neuropathic pain.

12. The method according to claim 1, wherein the pain is oncological pain.

13. The method according to claim 1, wherein the antibody has a long duration of action.

14. A kit comprising a composition containing a humanized anti-TrkA antibody capable of inhibiting the binding between NGF and TrkA, wherein the variable region of the antibody light chain comprises the sequence of SEQ ID NO:1 comprising all three complementarity determining regions (CDRs) having a sequence selected from aa. 24 to aa. 33 of SEQ ID NO: 1; from aa. 49 to aa. 55 of SEQ ID NO: 1; and from aa. 88 to aa. 96 of SEQ ID NO:1; and wherein the variable region of the antibody heavy chain comprises the sequence of SEQ ID NO: 2 comprising all three of the complementarity determining regions (CDRs) having a sequence selected from aa. 26 to aa. 35 of SEQ ID NO: 2; from aa. 50 to aa. 66 of SEQ ID NO: 2; from aa. 99 to aa. 112 of SEQ ID NO: 2; and variants of the sequence from aa. 99 to aa. 112 of SEQ ID NO: 2, and instructions directing administration of said composition to a subject in need of treatment and/or prevention of chronic pain.

* * * * *

SEQUENCE LISTING

```
<160> NUMBER OF SEQ ID NOS: 6

<210> SEQ ID NO 1
<211> LENGTH: 106
<212> TYPE: PRT
<213> ORGANISM: Mus musculus

<400> SEQUENCE: 1

Asp Ile Val Leu Thr Gln Ser Pro Ala Ile Met Ser Ala Ser Leu Gly
1               5                   10                  15

Glu Glu Val Thr Leu Thr Cys Ser Ala Ser Ser Val Ser Tyr Met
            20                  25                  30

His Trp Tyr Gln Gln Lys Ser Gly Thr Ser Pro Lys Leu Leu Ile Tyr
        35                  40                  45

Thr Thr Ser Asn Leu Ala Ser Gly Val Pro Ser Arg Phe Ser Gly Ser
    50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Ser Tyr Pro Trp Thr
                85                  90                  95
```

```
Phe Gly Gly Gly Thr Lys Leu Glu Ile Lys
                100                 105

<210> SEQ ID NO 2
<211> LENGTH: 123
<212> TYPE: PRT
<213> ORGANISM: Mus musculus

<400> SEQUENCE: 2

Glu Val Lys Leu Val Glu Ser Gly Gly Leu Val Gln Pro Gly Gly
1               5                   10                  15

Ser Leu Lys Leu Ser Cys Ala Ala Ser Gly Phe Thr Phe Ser Thr Tyr
                20                  25                  30

Thr Met Ser Trp Ala Arg Gln Thr Pro Glu Lys Arg Leu Glu Trp Val
            35                  40                  45

Ala Tyr Ile Ser Lys Gly Gly Ser Thr Tyr Tyr Pro Asp Thr Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Ala Arg Gly Ala Met Phe Gly Asn Asp Phe Phe Phe Pro Met Asp Arg
                100                 105                 110

Trp Gly Gln Gly Thr Ser Val Thr Val Ser Ser
                115                 120

<210> SEQ ID NO 3
<211> LENGTH: 213
<212> TYPE: PRT
<213> ORGANISM: Homo sapiens

<400> SEQUENCE: 3

Asp Ile Val Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
                20                  25                  30

His Trp Tyr Gln Gln Lys Pro Gly Gln Ala Pro Lys Leu Leu Ile Tyr
            35                  40                  45

Thr Thr Ser Asn Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Val Ala Thr Tyr Tyr Cys His Gln Trp Ser Ser Tyr Pro Trp Thr
                85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190
```

```
Cys Glu Val Thr His Gln Gly Leu Ser Ser Pro Val Thr Lys Ser Phe
            195                 200                 205

Asn Arg Gly Glu Cys
        210

<210> SEQ ID NO 4
<211> LENGTH: 453
<212> TYPE: PRT
<213> ORGANISM: Homo sapiens

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Thr Met Ser Trp Ala Arg Gln Ala Pro Gly Lys Gly Leu Glu Trp Val
            35                  40                  45

Ala Tyr Ile Ser Lys Gly Gly Ser Thr Tyr Tyr Pro Asp Thr Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ser Ala Val Tyr Tyr Cys
                85                  90                  95

Ala Arg Gly Ala Met Phe Gly Asn Asp Phe Phe Pro Met Asp Arg
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350
```

```
Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
    435                 440                 445

Leu Ser Pro Gly Lys
    450

<210> SEQ ID NO 5
<211> LENGTH: 453
<212> TYPE: PRT
<213> ORGANISM: Homo sapiens

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Thr Met Ser Trp Ala Arg Gln Ala Pro Gly Lys Gly Leu Glu Trp Val
        35                  40                  45

Ala Tyr Ile Ser Lys Gly Gly Gly Ser Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ser Ala Val Tyr Tyr Cys
                85                  90                  95

Ala Arg Gly Ala Met Phe Gly Asn Asp Phe Phe Phe Pro Met Asp Arg
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270
```

```
Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Ala Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 6
<211> LENGTH: 450
<212> TYPE: PRT
<213> ORGANISM: Homo sapiens

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Thr Met Ser Trp Ala Arg Gln Ala Pro Gly Lys Gly Leu Glu Trp Val
        35                  40                  45

Ala Tyr Ile Ser Lys Gly Gly Gly Ser Thr Tyr Tyr Pro Asp Thr Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Ser Ala Val Tyr Tyr Cys
                85                  90                  95

Ala Arg Gly Ala Met Phe Gly Asn Asp Phe Phe Pro Met Asp Arg
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

```
Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly
225             230                 235                     240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
            260             265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
450
```